United States Patent
Yamamoto

(10) Patent No.: US 8,359,926 B2
(45) Date of Patent: Jan. 29, 2013

(54) ULTRASONIC DIAGNOSTIC APPARATUS

(75) Inventor: Masa Yamamoto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 260 days.

(21) Appl. No.: 12/992,689

(22) PCT Filed: Apr. 27, 2009

(86) PCT No.: PCT/JP2009/058274
§ 371 (c)(1),
(2), (4) Date: Nov. 15, 2010

(87) PCT Pub. No.: WO2009/139286
PCT Pub. Date: Nov. 19, 2009

(65) Prior Publication Data
US 2011/0067498 A1    Mar. 24, 2011

(30) Foreign Application Priority Data
May 16, 2008    (JP) ................................. 2008-129453

(51) Int. Cl.
*G01N 29/00* (2006.01)
*A61B 8/00* (2006.01)

(52) U.S. Cl. ............. 73/632; 73/602; 600/437; 600/459
(58) Field of Classification Search .................... 73/632, 73/596, 618, 626; 600/437, 439, 443
See application file for complete search history.

(56) References Cited

U.S. PATENT DOCUMENTS

| | | | | |
|---|---|---|---|---|
| 6,709,392 B1 * | 3/2004 | Salgo et al. | ................... | 600/439 |
| 7,993,056 B2 * | 8/2011 | Amemiya | ..................... | 374/117 |
| 8,165,364 B2 * | 4/2012 | Roth et al. | ................... | 382/128 |
| 2009/0028211 A1 * | 1/2009 | Amemiya | ..................... | 374/117 |
| 2009/0054783 A1 * | 2/2009 | Shibata | .......................... | 600/459 |
| 2009/0213897 A1 * | 8/2009 | Amemiya | ..................... | 374/117 |
| 2012/0209119 A1 * | 8/2012 | Ohshima | ....................... | 600/443 |
| 2012/0238878 A1 * | 9/2012 | Tanabe | .......................... | 600/447 |

FOREIGN PATENT DOCUMENTS

| | | |
|---|---|---|
| JP | 05-245140 | 9/1993 |
| JP | 08-182673 | 7/1996 |
| JP | 10-118069 | 5/1998 |
| JP | 2005-253773 | 9/2005 |
| JP | 2005-288163 | 10/2005 |
| KR | 2007021417 | * 2/2007 |
| WO | 2004/089221 A1 | 10/2004 |

* cited by examiner

*Primary Examiner* — J M Saint Surin
(74) *Attorney, Agent, or Firm* — Brundidge & Stanger, P.C.

(57) ABSTRACT

An ultrasonic diagnostic apparatus in accordance with the invention includes: an ultrasonic probe configured to transmit an ultrasonic wave to an object to be tested and receiving an ultrasonic wave from the object; an ultrasonic transmitter/receiver configured to provide a signal that causes the ultrasonic probe to transmit an ultrasonic wave and signal-processing a signal received from the object by the ultrasonic probe; an ultrasonic image constructor configured to construct an ultrasonic image from the signal-processed received signal; an image display for displaying the ultrasonic image; a controller configured to control the ultrasonic transmitter/receiver, the ultrasonic image constructor and the image display to work properly; and a temperature sensor, provided on the ultrasonic probe, configured to sense the temperature of the ultrasonic probe and outputting the sensed temperature to the controller. The controller obtains the temperature variation rate of the ultrasonic probe from the temperature sensor, determines a usage state of the ultrasonic probe based on the obtained temperature variation rate, and controls the ultrasonic transmitter/receiver based on the determined usage state of the ultrasonic probe.

9 Claims, 8 Drawing Sheets

FIG. 3

| | |
|---|---|
| MONITORS PREPARATION STAGE BEFORE IMAGE CAPTURING | ☑ ON  /  ☐ OFF |
| THRESHOLD FOR PROBE TO BE RELEASED FROM FROZEN STATE TEMPERATURE VARIATION PER [3] SEC | + [3] °C  /  − [3] °C |
| THRESHOLD FOR PROBE TO BE PUT INTO FROZEN STATE TEMPERATURE VARIATION PER [3] SEC | + [3] °C  /  − [3] °C |

(SET DESIRED NUMBER IN [ ])

FIG. 4
(a)
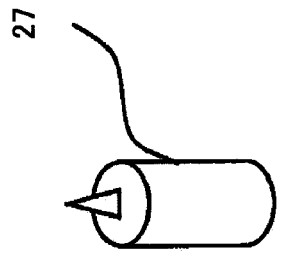
(b)
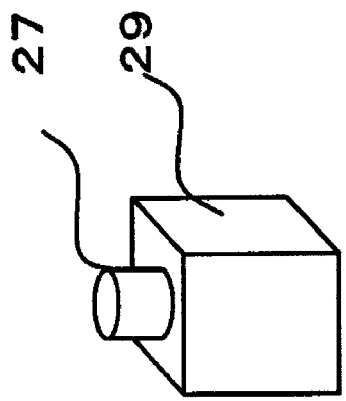

ULTRASONIC DIAGNOSTIC APPARATUS

TECHNICAL FIELD

The present invention relates to an ultrasonic diagnostic apparatus configured to transmit an ultrasonic wave to an object to be tested and receiving a reflected wave to obtain an echo image.

BACKGROUND ART

A conventional ultrasonic diagnostic apparatus has several probes. So, as a preparation stage before image capturing, an operator performs the following operations in random order for a probe to use:

Takes a probe appropriate for an area to diagnose from its holder,

Applies an ultrasonic gel to the vibrator surface of the probe,

Visually checks which connector of the main body of the ultrasonic diagnostic apparatus is connected to the probe, and Selects the probe by pushing a selection button for the probe connector, which releases the probe from a frozen state.

The probe can be selected by using a touch sensor included in the probe (see Patent Document 1) or a switch sensor disposed in the probe holder that detects that the probe is taken from the holder (see Patent Document 2).

Also, the conventional ultrasonic diagnostic apparatus may have a temperature manager that checks for a risk of low-temperature burns due to touching the probe surface, heated by ultrasonic transmission, to the body surface and performs other processings, using a temperature sensor included in the probe. For example, the temperature manager displays the temperature on a display and, when the temperature implies the risk, instructs a controller to change a parameter for ultrasonic transmission causing the temperature increase (see Patent Documents 3 and 4).

PRIOR ART DOCUMENT

Patent Document

Patent Document 1: JP-A-5-245140
Patent Document 2: JP-A-8-182673
Patent Document 3: JP-A-10-118069
Patent Document 4: JP-A-2005-253776

SUMMARY OF THE INVENTION

Problems to be Solved by the Invention

However, the conventional ultrasonic diagnostic apparatus needs the sensor to be additionally included for selecting the probe. Another problem is that the probe is also released from the frozen state when touching the probe or taking the probe from the probe holder for just moving or returning the probe rather than using the probe.

It is an object of the invention to provide an ultrasonic diagnostic apparatus that allows a probe to be selected and released from a frozen state without any particular operation just before image capturing.

Means for Solving the Problems

In order to achieve the above-described object, the invention obtains a temperature variation rate of an ultrasonic probe from a temperature sensor, determines a usage state of the ultrasonic probe based on the obtained temperature variation rate, and controls the ultrasonic transmitter/receiver to work based on the determined usage state of the ultrasonic probe.

Specifically, an ultrasonic diagnostic apparatus in accordance with the invention includes: an ultrasonic probe configured to transmit an ultrasonic wave to an object to be tested and receiving an ultrasonic wave from the object; an ultrasonic transmitter/receiver configured to provide a signal that causes the ultrasonic probe to transmit an ultrasonic wave and signal-processing a signal received from the object by the ultrasonic probe; an ultrasonic image constructor configured to construct an ultrasonic image from the signal-processed received signal; an image display for displaying the ultrasonic image; a controller configured to control the ultrasonic transmitter/receiver, the ultrasonic image constructor and the image display to work properly; and a temperature sensor, provided on the ultrasonic probe, configured to sense the temperature of the ultrasonic probe and outputting the sensed temperature to the controller. The controller is characterized by obtaining the temperature variation rate of the ultrasonic probe from the temperature sensor, determining a usage state of the ultrasonic probe based on the obtained temperature variation rate, and controlling the ultrasonic transmitter/receiver based on the determined usage state of the ultrasonic probe.

According to the ultrasonic diagnostic apparatus of the invention, the controller obtains a temperature variation rate of the ultrasonic probe from the temperature sensor, determines a usage state of the ultrasonic probe based on the obtained temperature variation rate, and controls the ultrasonic transmitter/receiver based on the determined usage state of the ultrasonic probe, which allows a probe to be selected and released from a frozen state without any particular operation just before image capturing.

Advantage of the Invention

According to the invention, an ultrasonic diagnostic apparatus can be provided that allows a probe to be selected and released from a frozen state without any particular operation just before image capturing.

BRIEF DESCRIPTION OF THE DRAWINGS

FIG. 3 An illustration showing a setting on a control panel 15 in accordance with the embodiment.

FIG. 4 An illustration showing an ultrasonic gel 27 in accordance with the embodiment.

MODE FOR CARRYING OUT THE INVENTION

An embodiment of the invention is described in detail below with reference to the drawings.

An ultrasonic diagnostic apparatus 1 in accordance with the embodiment is described.

Figure 1:
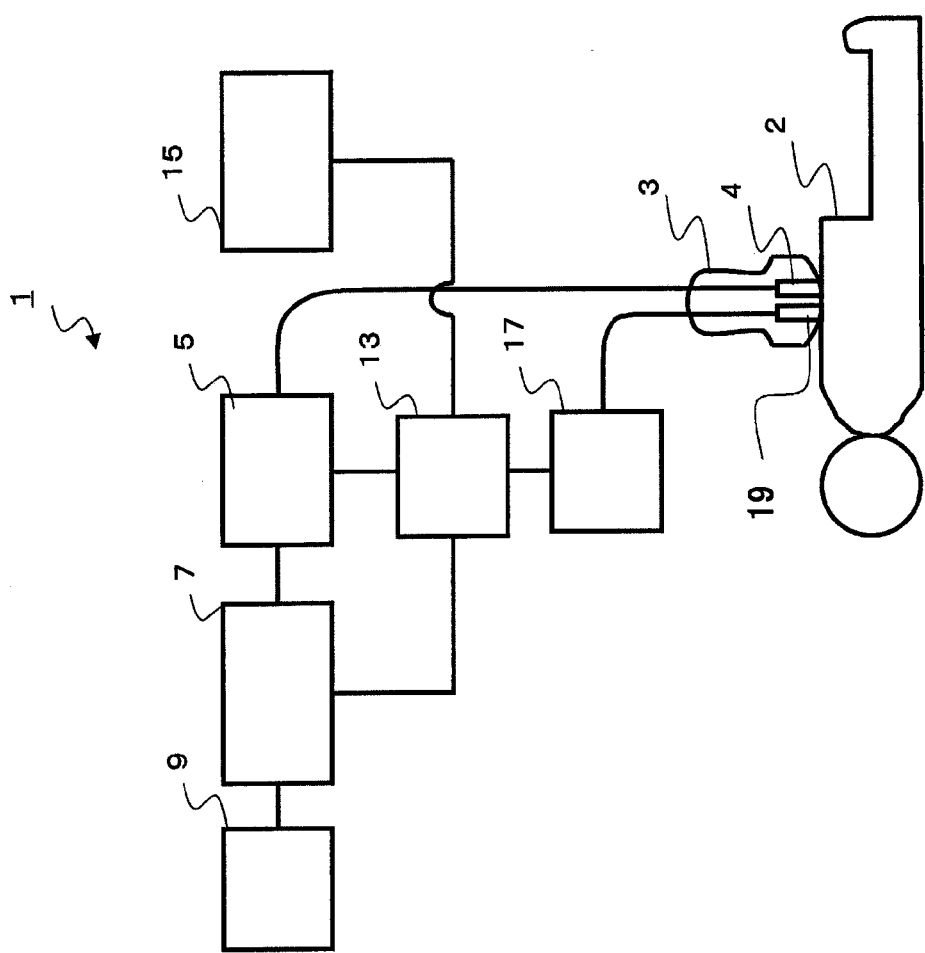
FIG. 1 A block diagram of an ultrasonic diagnostic apparatus 1 in accordance with an embodiment of the invention.

FIG. 1 is a block diagram showing a configuration of the ultrasonic diagnostic apparatus 1. The ultrasonic diagnostic apparatus 1 transmits and receives an ultrasonic wave into and from an object to be tested 2, and uses an obtained reflected echo signal to form and display a two- or three-dimensional ultrasonic image for an area to diagnose. The ultrasonic diagnostic apparatus 1 includes: an ultrasonic probe 3 including a vibrator 4 configured to irradiate the object 2 with an ultrasonic wave and to receive an ultrasonic wave from the object 2 and a surface temperature sensor 19 configured to monitor the temperature of the probe surface to be touched to the object; an ultrasonic transmitter/receiver 5 configured to transmit a signal that causes the vibrator 4 to generate an ultrasonic wave and to process an ultrasonic wave received by the vibrator 4; an ultrasonic image constructor 7 configured to construct a two-dimensional ultrasonic image (B-mode image) or three-dimensional ultrasonic image based on the received signal; a display 9 for displaying the ultrasonic image constructed by the ultrasonic image constructor 7; a controller 13 configured to control various components; a control panel 15 as operation unit from which an operator can give an instruction to the controller 13; and a temperature manager 17 configured to obtain temperature information from the surface temperature sensor 19 of the probe 3 to monitor the probe surface temperature and outputting a control signal to the controller 13 as appropriate.

The control panel 15 is an interface operated by the operator to input various control parameters to the controller 13, with which it can be determined whether probe monitoring process is to be performed or not, and the thresholds of the temperature variation can be determined for use in deciding whether or not the probe 3 is to be released from a frozen state or whether or not the probe 3 is to be put into the frozen state, as shown in FIG. 3.

The temperature manager 17 checks for a risk of low-temperature burns due to touching the probe surface, heated by ultrasonic transmission, to the body surface and performs other processings. For example, the temperature manager 17 communicates the temperature to the controller 13 to display on the display 9 and, when the temperature implies the risk, instructs the controller 13 to change a parameter for ultrasonic transmission causing the temperature increase.

In the invention, the surface temperature sensor 19 works even in the frozen state, and then the temperature manager 17 monitors the surface temperature of the probe 3 to determine whether or not it is in a preparation stage before or after image capturing.

Figure 2:
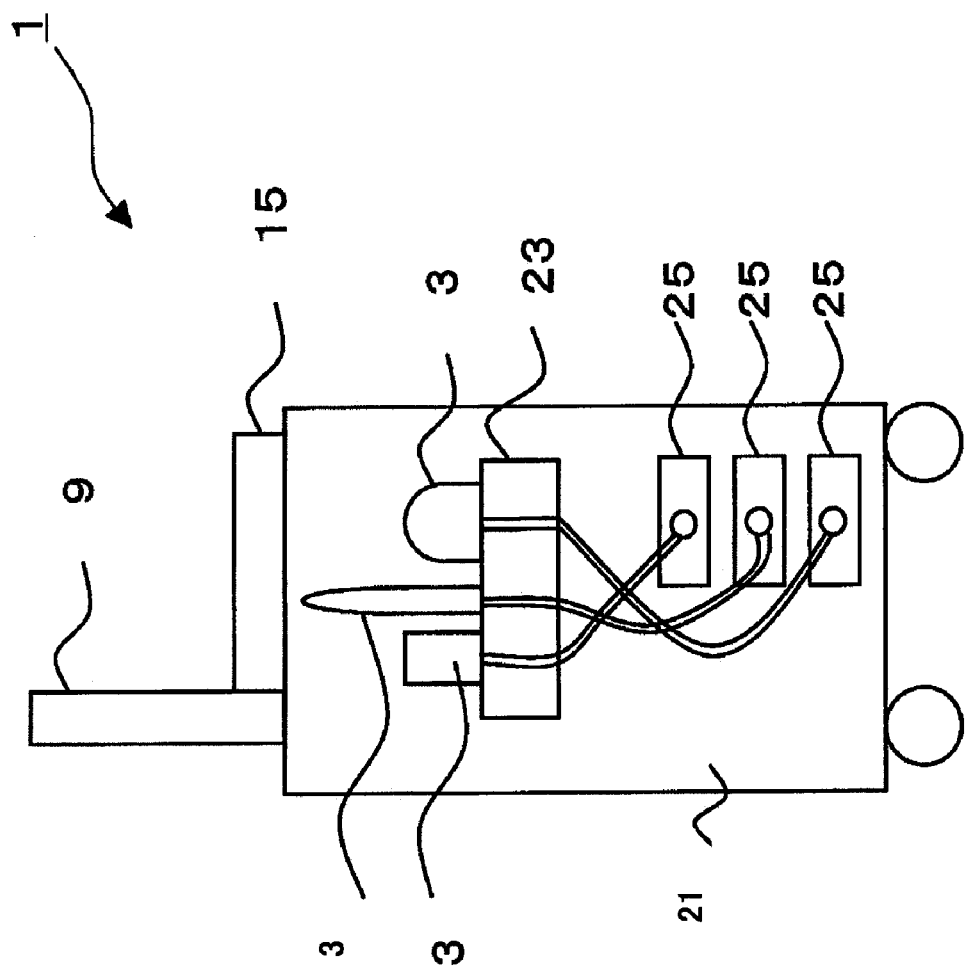
FIG. 2 An illustration generally showing an appearance of the ultrasonic diagnostic apparatus 1 in accordance with the embodiment.

FIG. 2 generally shows an appearance of the ultrasonic diagnostic apparatus 1. A main body 21 includes therein the ultrasonic transmitter/receiver 5, the ultrasonic image constructor 7, the controller 13 and the temperature manager 17. The main body 21 further includes thereon the display 9 and the control panel 15. Typically one or several probes 3 are connected to the main body 21 via probe connectors 25. The probes 3, each including the ultrasonic vibrator 4 on the tip, are hung on probe holders 23.

Before image capturing with the ultrasonic diagnostic apparatus 1, an ultrasonic gel 27 is applied to an area in which the surface of the probe 3 is touched to the body surface of the object 2. The ultrasonic gel 27 is for removing air so as not to prevent ultrasonic transmission. The ultrasonic gel 27 may be kept near the apparatus in a room temperature, as shown in FIG. 4(*a*). Or the ultrasonic gel 27 may be kept near the apparatus, warmed in a gel warmer 29 so as not to make the object feel cold when the ultrasonic gel 27 is touched to the body surface of the object in diagnosing, as shown in FIG. 4(B).

Then, in the preparation stage before image capturing, the operator applies the ultrasonic gel 27 to the surface of the probe 3 and touches the surface of the probe 3 to the object 2. Note that the operator may also apply the ultrasonic gel 27 directly to the body surface of the object 2 which is appropriate as an area to be tested and smooth out the applied ultrasonic gel 27 on the body surface of the object 2 using the probe 3.

Figure 6:
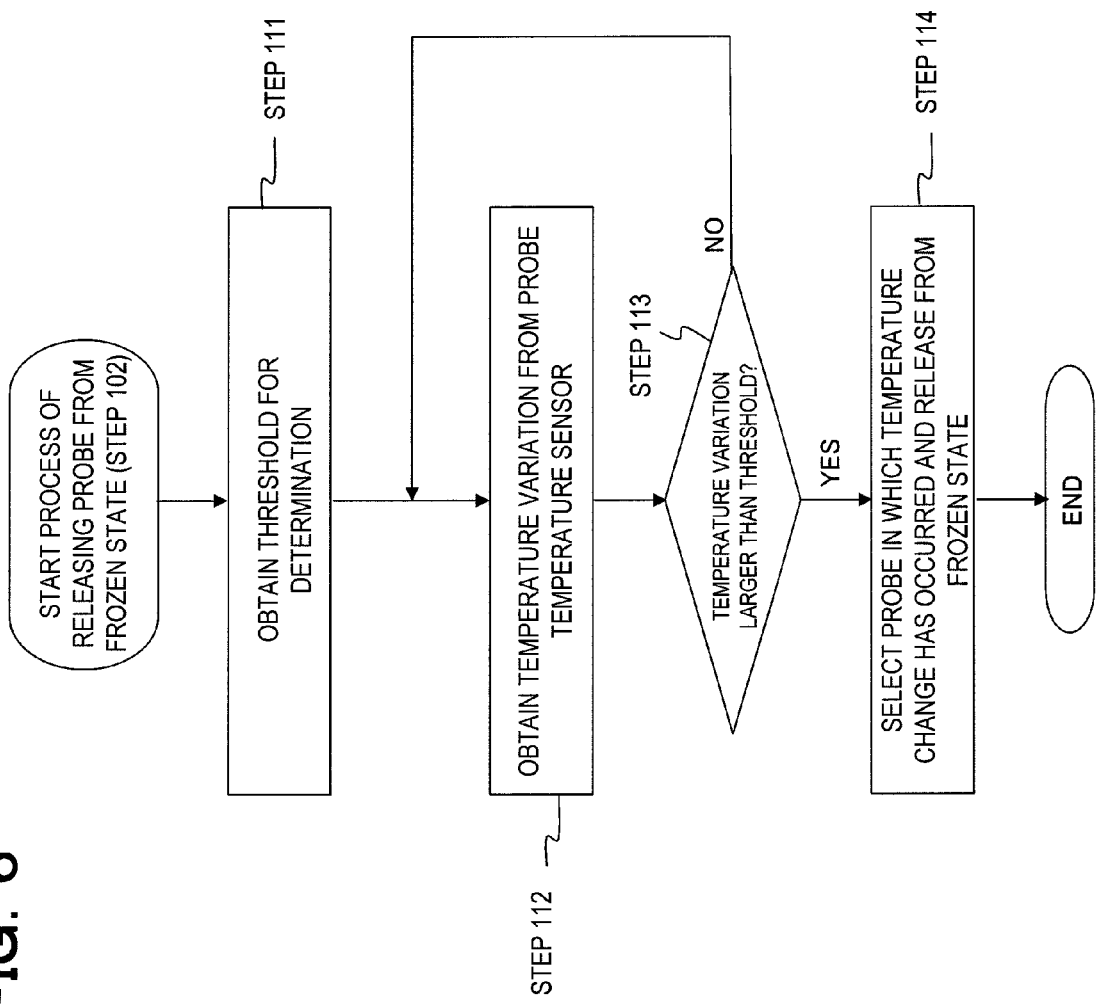
FIG. 6 A flowchart describing how the ultrasonic diagnostic apparatus 1 works in a process of releasing a probe from a frozen state (step 102).
Figure 7:
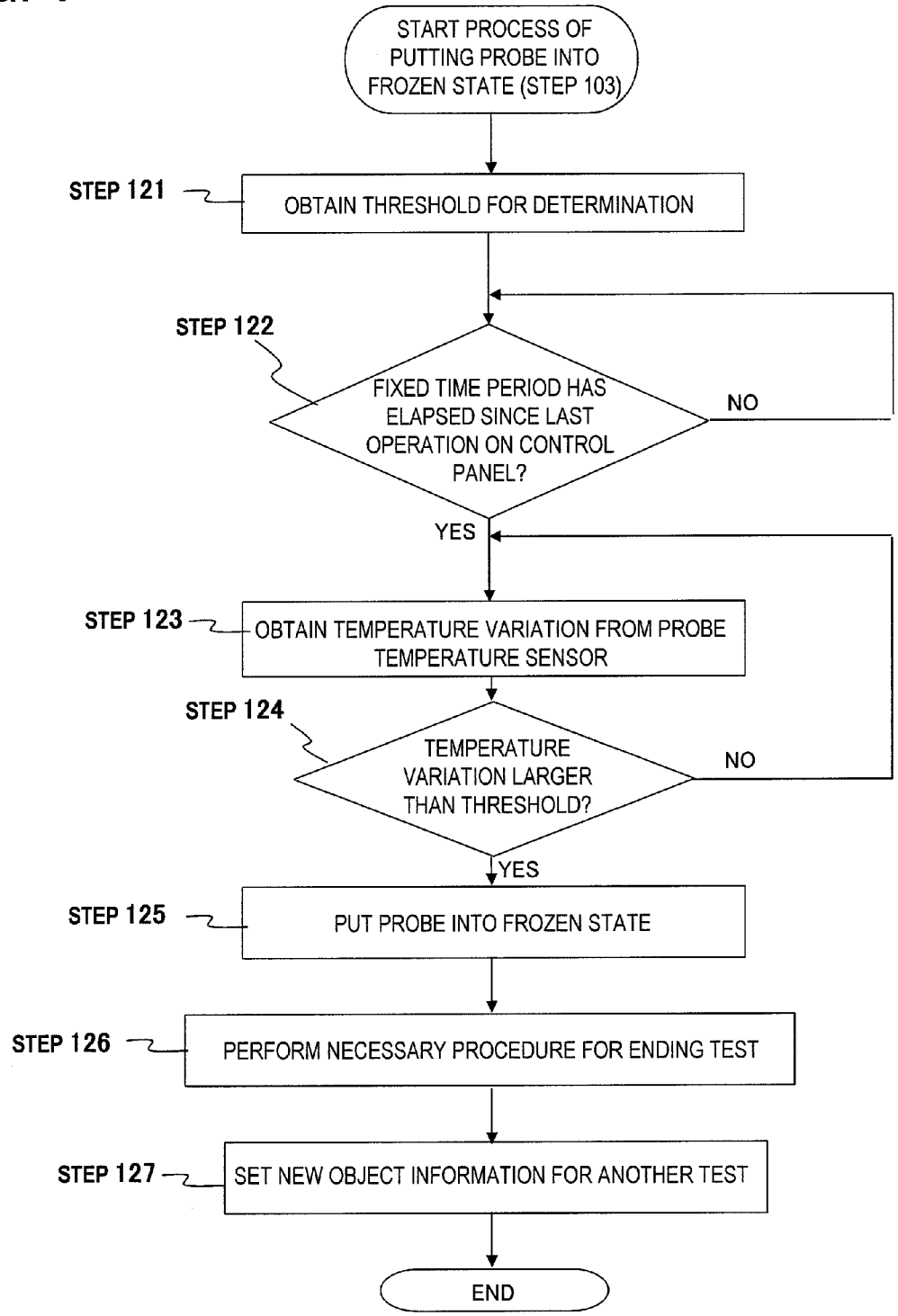
FIG. 7 A flowchart describing how the ultrasonic diagnostic apparatus 1 works in a process of putting the probe into the frozen state (step 103).

Next, how the ultrasonic diagnostic apparatus 1 works is described with reference to FIGS. 5 to 7.

Figure 5:
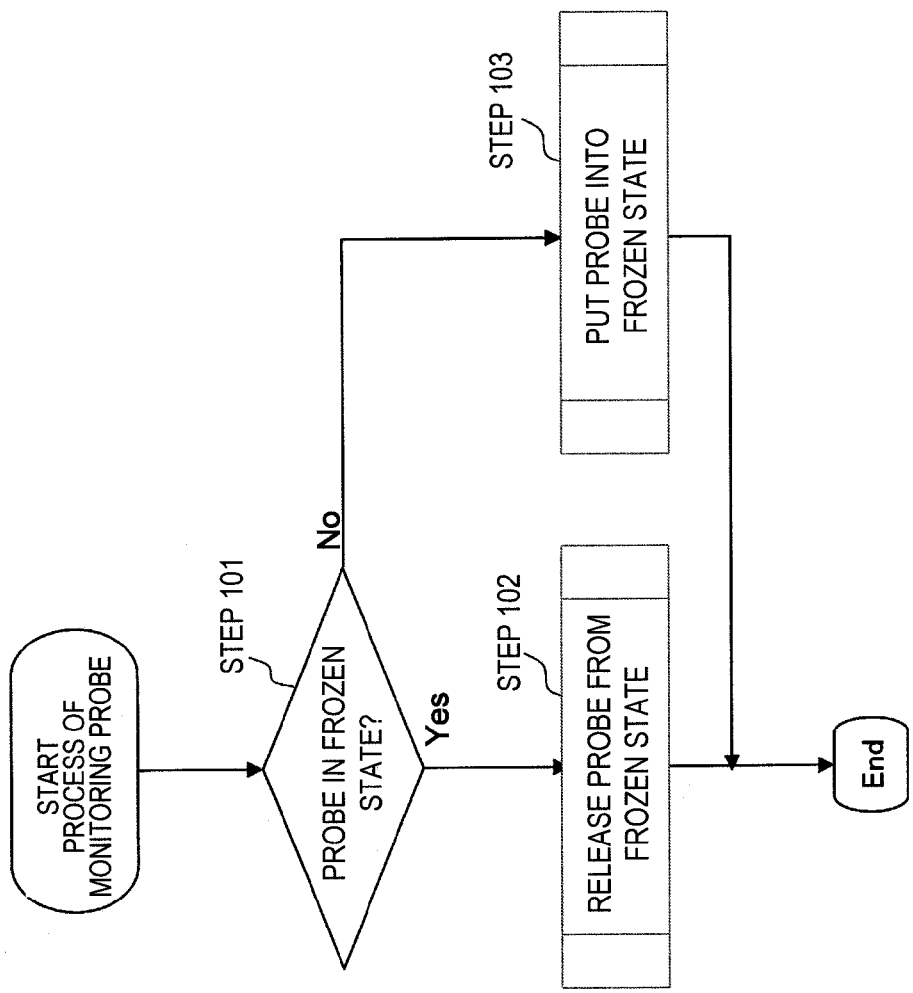
FIG. 5 A flowchart describing how the ultrasonic diagnostic apparatus 1 works in probe monitoring.

First, as shown in FIG. 5, the ultrasonic diagnostic apparatus 1 determines whether or not the probe 3 is in the frozen state (step 101). If the ultrasonic diagnostic apparatus 1 determines that the probe 3 is in the frozen state (YES in step 101), the ultrasonic diagnostic apparatus 1 proceeds to release the probe 3 from the frozen state (step 102). On the other hand, if the ultrasonic diagnostic apparatus 1 determines that the probe 3 is not in the frozen state (NO in step 101), the ultrasonic diagnostic apparatus 1 proceeds to put the probe 3 into the frozen state (step 103).

Next, a process of releasing the probe 3 from the frozen state (step 102) is described with reference to FIG. 6. First, the ultrasonic diagnostic apparatus 1 obtains a threshold for use in determining whether or not it is in the preparation stage before image capturing (step 111). This threshold may be preset by the apparatus or may be set by the operator through the control panel 15 as shown in FIG. 3. The ultrasonic diagnostic apparatus 1 measures the surface temperature of the probe 3 through the surface temperature sensor 19 to obtain the temperature variation (step 112). The temperature variation (the time rate of temperature change) is obtained by, for example, measuring the surface temperature at regular time intervals, saving a few seconds or a few minutes of the latest measurements, and obtaining the temperature variation during a time period to be determined.

The temperature variation may be not only the difference between the first and last values within a fixed time period, but also a statistic such as an accumulated amount of changes within a fixed time period.

The ultrasonic diagnostic apparatus 1 determines whether or not the temperature variation is larger than the threshold (step 113). If the temperature variation is smaller than the threshold (NO on step 113), the ultrasonic diagnostic apparatus 1 repeats the step 112 to obtain a new temperature variation. On the other hand, if the temperature variation is larger than the threshold (YES in step 113), the ultrasonic diagnostic apparatus 1 determines that it is in the preparation stage before image capturing, then selects the probe 3 in which temperature change has occurred and releases the probe 3 from the frozen state to be put into an operational state (step 114).

Note that this process may be set to be performed only when the operator selects this capability through the control panel 15 or may be set to be automatically performed when the probe has been in the frozen state for a fixed time period.

Also, after it is determined that it is in the preparation stage before image capturing, if an end-test key is pressed to end the test or if any panel operation has not been performed for a fixed time period, a screen for entering an object information such as an object ID or name may be displayed before the probe is automatically selected or released from the frozen state.

This is because it can be determined that the object has been changed after the end-test key was pressed to end the test and a procedure for ending the test was performed, or even when, without the above operation, the control panel has not been operated for a fixed time period. Thus, automatically displaying the screen prompting the operator to enter a new object information when it is determined that the object has been changed can further simplify the operation of the operator before diagnosing. In this case, when the screen for entering the object information is ended, the probe is automatically selected and released from the frozen state.

Next, a process of putting the probe 3 into the frozen state (step 103) is described with reference to FIG. 7. First, the ultrasonic diagnostic apparatus 1 obtains a threshold for use in determining whether or not it is in the preparation stage after image capturing (step 121). This threshold may be preset by the apparatus or may be set by the operator through the control panel 15 as shown in FIG. 3. The ultrasonic diagnostic apparatus 1 determines whether or not a fixed time period has elapsed since the last operation on the control panel 15, such as changing a measurement mode (step 122). If determined that the fixed time period has not elapsed yet (NO in step 122), the ultrasonic diagnostic apparatus 1 waits until the fixed time period elapses. On the other hand, if determined that the fixed time period has elapsed, the ultrasonic diagnostic apparatus 1 obtains the temperature variation from the measured surface temperature of the probe 3 (step 123). The temperature variation can be determined in a way similar to step 112.

The probe surface temperature may also change due to an operation such as mode change or frequency change during the test. So, in order to distinguish the state to be detected after image capturing from other states, step 122 is provided not to put the probe into the frozen state if a panel operation has been performed in a fixed time period.

The ultrasonic diagnostic apparatus 1 determines whether or not the temperature variation is larger than the threshold (step 124). If the temperature variation is smaller than the threshold (NO on step 124), the ultrasonic diagnostic apparatus 1 repeats the step 112 to obtain a new temperature variation. On the other hand, if determined that the temperature variation is larger than the threshold (YES on step 124), the ultrasonic diagnostic apparatus 1 determines that it is in the preparation stage after image capturing, then puts the probe 3 in which temperature change has occurred into the frozen state (step 125). Then, the ultrasonic diagnostic apparatus 1 performs the necessary procedure for ending the test (step 126) and sets a new object information for another test (step 127).

The necessary procedure for ending the test to be performed in step 126 includes transforming obtained measurement data into a file format for storage, transferring image data and measurement data to a server, and deleting temporary files for image data and measurement data. The new object information for another test to be set in step 127 is obtained from a Radiology Information System (RIS). Or a screen for entering the new object information is automatically displayed and other preparations for another test are performed.

The process of putting the probe 3 into the frozen state is useful when the ultrasonic diagnostic apparatus 1 is left unused with the probe 3 released from the frozen state or when wiping the ultrasonic gel off the surface of the probe 3 released from the frozen state.

In general, the surface temperature of the probe 3 is increased by ultrasonic transmission when the probe 3 is released from the frozen state. During image capturing, since the probe 3 is touched to the body surface of the object 2, the gradient of the temperature increasing curve of the probe 3 is reduced to some extent by heat absorption of the body surface. On the other hand, when the probe 3 is left in the air, released from the frozen state, the gradient of the temperature increasing curve of the probe 3 becomes larger without heat absorption of the body surface. From this difference in the gradient, it can be determined whether or not the ultrasonic diagnostic apparatus 1 is left unused.

Note that, as for the threshold obtained in steps 111 and 121, the threshold having a different temperature change curve for each probe is desirably obtained because an ultrasonic transmission parameter is different for each probe.

Figure 8:
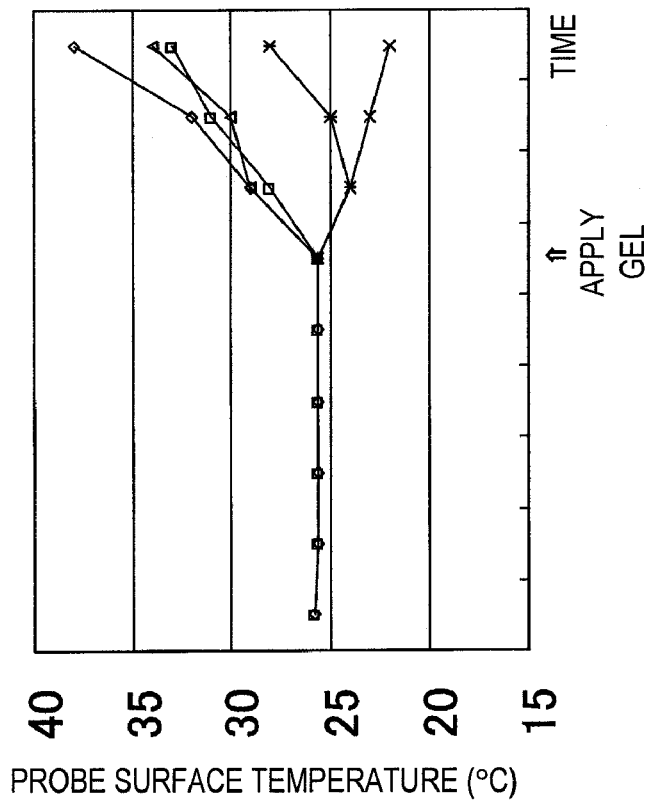
FIG. 8 A chart showing the temperature change of the probe in accordance with the embodiment.

Next, the surface temperature change over time of the probe is described with reference to FIG. 8. FIG. 8 shows the surface temperature change over time of the probe.

The probe before being applied with the ultrasonic gel is left in the frozen state. The surface temperature of the probe in this state reflects the change in the room temperature and is almost constant or changes gently according to the change in the room temperature. When the ultrasonic gel is applied in the preparation stage before image capturing or when the probe surface is touched to the body surface, the surface temperature change becomes larger than that of the probe left before being applied with the ultrasonic gel.

As shown by (a) to (e) in FIG. 8, the surface temperature change varies depending on how the ultrasonic gel is stored or whether or not the probe is touched to the object, but, at any rate, differs from that of the probe left in the frozen state before being applied with the ultrasonic gel. According to the invention, the temperature variation over time is monitored to detect the transition from the unused state to the preparation stage before image capturing and perform a necessary procedure.

Note that FIG. 8 shows the surface temperature change of the probe 3 when a certain time period has elapsed since the end of diagnosing. The surface temperature of the probe just after the end of diagnosing is gently decreased by heat dissipation from the surface temperature increased by ultrasonic transmission, which shows a different change from the above case. However, also in this case, this temperature change is different from that after applying the gel, so the transition to the preparation stage before image capturing can be identified.

While the embodiment has been described with reference to the surface temperature of the ultrasonic probe, the invention is not limited to measuring the surface temperature as long as the temperature of the ultrasonic probe can be measured.

According to the embodiment, the operator can start image capturing without selecting the probe and releasing the probe from the frozen state, which need to be performed in the preparation stage before image capturing. This is effective in reducing the amount of operation by the operator.

According to the embodiment, the probe can be released from the frozen state only by applying the ultrasonic gel, which allows diagnosing to be quickly started, increasing the efficiency of intraoperative diagnosis. Also, keyboard-free operation can reduce the stress of the operator.

When image capturing needs to be continued without any panel operation, such as in intraoperative image capturing, conventionally, a user needs to disable the function of automatically putting the probe into the frozen state. However, according to the invention, whether image capturing is continuing or not can be determined even without any panel operation, eliminating the need for enabling or disabling the function by the user.

Further, according to the embodiment, an additional sensor need not be provided, which allows the invention to be applied to a low-cost, compact and hand-carriable apparatus.

Although the preferred embodiment of the ultrasonic diagnostic apparatus in accordance with the invention has been described with reference to the accompanying drawings, the invention is not limited to this embodiment. It is apparent to the person skilled in the art that various variations and modifications can be conceived without departing from the scope of the technical spirit disclosed herein, and also it is understood that those variations and modifications naturally fall within the technical scope of the invention.

DESCRIPTION OF REFERENCE NUMERALS AND SIGNS 1 ultrasonic diagnostic apparatus, 2 object to be tested, 3 probe, 5 ultrasonic transmitter/receiver, 7 ultrasonic image constructor, 9 display, 13 controller, 15 control panel, 17 temperature manager, 19 surface temperature sensor, 21 main body, 23 probe holders, 25 probe connectors, 27 ultrasonic gel, 29 gel warmer

The invention claimed is:

1. An ultrasonic diagnostic apparatus comprising:
an ultrasonic probe configured to transmit an ultrasonic wave to an object to be tested and receiving an ultrasonic wave from the object;
an ultrasonic transmitter/receiver configured to provide a signal that causes the ultrasonic probe to transmit an ultrasonic wave and signal-processing a signal received from the object by the ultrasonic probe;
an ultrasonic image constructor configured to construct an ultrasonic image from the signal-processed received signal;
an image display configured to display the ultrasonic image;
a controller configured to control the ultrasonic transmitter/receiver, the ultrasonic image constructor and the image display to work properly; and
a temperature sensor, provided on the ultrasonic probe, configured to sense the temperature of the ultrasonic probe and outputting the sensed temperature to the controller,
wherein the controller obtains the temperature variation rate of the ultrasonic probe from the temperature sensor, determines a usage state of the ultrasonic probe based on the obtained temperature variation rate, and controls the ultrasonic transmitter/receiver based on the determined usage state of the ultrasonic probe.

2. The ultrasonic diagnostic apparatus according to claim 1, wherein the usage state of the ultrasonic probe is at least one of a state of having started using the ultrasonic probe and a state of having ended use of the ultrasonic probe.

3. The ultrasonic diagnostic apparatus according to claim 1, wherein the controller compares a threshold corresponding to a preset temperature variation rate with an actual temperature variation rate to determine the usage state of the ultrasonic probe.

4. The ultrasonic diagnostic apparatus according to claim 3, wherein, based on the comparison result, the controller controls the ultrasonic image constructor to enable at least one of the state of having started using the ultrasonic probe and the state of having ended use of the ultrasonic probe.

5. The ultrasonic diagnostic apparatus according to claim 3, further comprising a storage for storing a threshold corresponding to a temperature variation rate,
wherein the controller compares a threshold corresponding to the temperature variation stored in the storage with an actual temperature variation.

6. The ultrasonic diagnostic apparatus according to claim 1, further comprising a setting unit with which an operator sets a control parameter for the controller,
wherein the controller compares a threshold corresponding to the temperature variation rate set by the setting unit with an actual temperature variation rate to determine the usage state of the ultrasonic probe.

7. The ultrasonic diagnostic apparatus according to claim 6, wherein, based on the comparison result, the controller controls the ultrasonic image constructor to enable at least one of the state of having started using the ultrasonic probe and the state of having ended use of the ultrasonic probe.

8. The ultrasonic diagnostic apparatus according to claim 6, further comprising a storage configured to store a threshold corresponding to the temperature variation,
wherein the controller compares a threshold corresponding to the temperature variation stored in the storage with an actual temperature variation.

9. The ultrasonic diagnostic apparatus according to claim 6, wherein the setting unit sets whether or not the ultrasonic transmitter/receiver is to be controlled to control the controller to enable at least one of the state of having started using the ultrasonic probe and the state of having ended use of the ultrasonic probe.

* * * * *